United States Patent [19]

Rounds

[11] Patent Number: 4,786,589

[45] Date of Patent: Nov. 22, 1988

[54] IMMUNOASSAY UTILIZING FORMAZAN-PRELABELED REACTANTS

[75] Inventor: Donald E. Rounds, Altadena, Calif.

[73] Assignee: Huntington Medical Research Institute, Pasadena, Calif.

[21] Appl. No.: 897,601

[22] Filed: Aug. 18, 1986

[51] Int. Cl.⁴ ............... G01N 33/544; G01N 33/542; G01N 33/536

[52] U.S. Cl. .......................................... 435/5; 435/26; 435/805; 435/810; 435/7; 436/528; 436/530; 436/536; 436/537; 436/541; 436/805; 436/807; 436/810

[58] Field of Search ............... 436/528, 530, 536, 537, 436/541, 805, 807, 810; 435/7, 26,5, 805, 810

[56] References Cited

U.S. PATENT DOCUMENTS

| | | | |
|---|---|---|---|
| 450,649 | 12/1885 | Saxena | 435/7 |
| 2,111,976 | 3/1938 | Laughlen | 435/7 |
| 2,301,717 | 11/1942 | Terry | 435/29 |
| 3,011,874 | 12/1961 | Deutsch | 435/12 |
| 3,876,504 | 4/1975 | Koffler | 435/7 |
| 3,949,065 | 4/1976 | Forgione | 435/7 |
| 4,168,146 | 9/1979 | Grubb | 435/7 |
| 4,181,560 | 1/1980 | Maier, Jr. | 436/537 |
| 4,200,690 | 4/1980 | Root | 435/7 |
| 4,254,222 | 3/1981 | Owen | 435/26 |
| 4,271,265 | 6/1981 | Deneke | 435/16 |
| 4,302,536 | 11/1981 | Longenecker | 435/7 |
| 4,373,932 | 2/1983 | Gribnau | 436/501 |
| 4,429,050 | 1/1984 | Yasuda et al. | 436/541 |
| 4,446,238 | 1/1984 | DeMey | 436/527 |
| 4,472,498 | 9/1984 | Masuda | 435/7 |
| 4,595,661 | 6/1986 | Cragle | 436/534 |
| 4,613,569 | 9/1986 | Geisler | 435/26 |
| 4,637,978 | 1/1987 | Dappen | 435/11 |
| 4,639,419 | 1/1987 | Olson | 435/5 |
| 4,654,300 | 3/1987 | Zuk et al. | 436/534 |
| 4,703,017 | 10/1987 | Campbell et al. | 436/501 |

OTHER PUBLICATIONS

Article: AuroProbe BL (AR).
Article: AuroProbe LM (AS).
Article: AuroProbe EM (EM).
Article: Immunocytochemistry (AU).
Green et al, "Rapid Colormetric Assay for Cell Viability: Application to the Quantitation of Cytotoxic and Growth Inhibitory Lymphokines", J. Immunol. Methods 70:257–268 (May 25, 1984).

*Primary Examiner*—Christine M. Nucker
*Attorney, Agent, or Firm*—Christie, Parker & Hale

[57] ABSTRACT

An immunoassay procedure utilizing a formazan-labeled primary antibody to detect the presence of an antigen is disclosed. The formazan-labeled antibody is dissolved in a test fluid suspected to containing the antigen. A dipstick having a first section on which primary antibodies are bonded and a second section free of primary antibodies and antigens and blocked to prevent bonding of primary antibodies and antigens is immersed in the test fluid and removed after a select period of time. A difference in color between the first and second sections indicate the presence of the antigen.

18 Claims, No Drawings

IMMUNOASSAY UTILIZING FORMAZAN-PRELABELED REACTANTS

FIELD OF THE INVENTION

This invention relates to immunoassay techniques, and in particular, to a one step immunoassay procedure involving reactants prelabeled with formazan.

BACKGROUND OF THE INVENTION

In recent years highly sensitive immunoassay techniques have been developed which detect dilute antigen-antibody reactions. These include radio-immunoassay (RIA) in which a reactant is labeled with radioactive iodine, fluorescence immunoassay (FIA) in which the label is a fluorescent dye, and enzyme linked immunosorbant assay (ELISA) in which a reactant is conjugated with an enzyme which catalyzes a color-forming biochemical reaction after the immunochemical reaction has been completed. In each case, the product formed by the antibody-antigen reaction is separated, for example, by binding the reaction product to another antibody which, in turn, is bound to an immobilized membrane. Once separated, the antibody-antigen reaction product can be detected and analyzed.

The first two types of immunoassay procedure described above, i.e., radio-immunoassay and fluorescence immunoassay, require specialized equipment even for qualitative analysis and therefore cannot be used at home, or in doctors' offices or laboratories that do not have that specialized equipment. The ELISA method enables visualization of the reaction product but often requires multiple lengthy incubation periods to develop adequate color intensity for the visualization. Such a multi-step procedure enhances the risk of error, particularly when the procedure is conducted by an unskilled person.

A fourth type of immunoassay procedure has resulted from prelabeling reactants with colloidal gold. The reaction product has a relatively weak optical density in the visible spectrum and requires enhancement, e.g., by a subsequent silver staining procedure for most visual applications. Because colloidal gold is electron opaque, this method is valuable for use in electron microscopy.

SUMMARY OF THE INVENTION

The present invention provides a simple immunoassay procedure for detecting the presence of a specific protein, e.g., an antibody, antigen or the like, in a test fluid. The procedure comprises mixing a sample of the test fluid with a prelabeled primary protein having a specific affinity for the protein to be detected. The primary protein is prelabeled either directly or indirectly with a protein-specific dye, preferably a formazan compound. Any reaction product formed is then separated from the unreacted prelabeled primary protein and can be detected visually, because of the color of the protein specific dye, without the aid of specialized equipment.

In a preferred embodiment of the invention, the system is provided as a one-step immunodot procedure for detecting specific proteins, e.g., antigens. In the procedure, primary antibodies prelabeled with a protein specific dye, preferably a formazan compound, are mixed with a sample of a fluid to be tested for the presence of the antigen. A solid substrate, e.g., a dipstick, comprising a membrane having a first section on which nonlabeled primary antibodies specific for the antigen have been bonded and a second section free of primary antibodies and antigens and blocked to prevent bonding of primary antibodies and antigens is immersed in the mixture. In a particularly preferred embodiment of the invention, a third section is provided on which the protein to be detected, e.g., the antigen, is bound. In such an embodiment, the second section serves as a negative control and the third section serves as a positive control. The substrate is withdrawn from the mixture after a selected period of time or after the reaction is complete as determined by visual inspection. A difference in color intensity between the first section and the second section indicates the presence of the antigen in the test fluid. Moreover, the magnitude of the difference in color intensity between the first and the second sections can be compared against the difference in color intensity developed with one or more samples having a known quantity of the antigen to determine at least an approximate amount of antigen in the test sample.

DETAILED DESCRIPTION

In a preferred embodiment of the invention there is provided a one-step dipstick immunodot procedure for detecting the presence of a wide variety of antigens. Such a procedure has a variety of applications, including detection of beta-human chorionic gonadotropin hormone in a urine sample to indicate pregnancy; detection of HTLV III virus, an indicator of acquired immune deficiency syndrome (AIDS); of herpes simplex virus—type II, an indicator of genital herpes, and the like. Other antigens detectable by this procedure include streptococcus A, feline leukemia virus, psittacosis virus, nuclear, thyroidal, mitochondrial, and smooth muscle antigens, treponema pallidum, cytomegalo virus, and numerous other viral and bacterial infections and tumor cell markers.

In the procedure, a formazan-labeled antibody having a specific affinity for a certain antigen is dissolved in a sample of a test fluid, e.g., blood serum, urine, etc., suspected of containing that antigen. A dipstick on which a nitrocellulose membrane is mounted is immersed in the reaction mixture. the membrane has one section on which nonlabeled antibodies having a specific affinity for that antigen are bonded. A second section is free of antibodies and antigen and blocked with a nonreactive protein to prevent bonding of formazanlabeled antibodies to the membrane. A third section is provided on which the antigen is bound. Reactions take place between the free antigen in the test fluid and the nonlabeled antibody bonded to the membrane as well as the free antigen and formazanlabeled antibody. This results in a sandwich of nonlabeled bonded antibody/antigen/formazan-labeled antibody over the first section of the membrane. A reaction also takes place between the formazan-labeled antibody and the bound antigen over the third section. No reaction takes place over the second section of the membrane.

The reaction is allowed to proceed for a fixed period of time or until completion as determined visually. Since formazan is a highly colored dye, the reacted formazan-labeled antibody imparts color to the third section, and if the antigen is present in the test fluid, to the first section. Since no reaction takes place over the second section, no color is developed over that section. The second section thus acts as a negative control.

In practice, it has been found that some background color is imparted across the entire membrane, including the second section due to absorption of unreacted formazan particles and, to a minor extent, of unreacted formazan-labeled antibody. Such background color is difficult to completely eliminate. Accordingly, presence of the antigen is indicated by a difference in color between the first and second sections of the membrane. The third section is provided as a positive control, the color which is developed showing that the appropriate reactions are in fact taking place.

The concentration of formazan-labeled primary antibody reactant in the test mixture is selected to yield a distinct color difference between the first and second sections of the dipstick membrane if a certain desired minimum concentration of antigens are present in the test fluid. It is therefore desirable to maximize the formation of formazan-labeled antibody-antigen conjugates which bind to the dipstick and, hence, maximize the development of color due to the antibody-antigen reaction while minimizing the intensity of the background color generated primarily by unreacted formazan in the reactant solution. Accordingly, it is preferred that the formazan-labeled antibody be prepared in such a manner which minimizes the amount of unreacted or unbound formazan in the reagent solution.

The length of time that the dipstick is immersed in the mixture is that which allows a difference in color intensity to develop between the first and second sections of the membrane if the antigen is present. For most antibody-antigen reactions, color development is essentially complete within 30 to 60 minutes.

If desired, color development of the dipstick can be monitored by simply removing the dipstick, visually checking the color intensity across the first section of the membrane and then reimmersing the dipstick. When no further change in color intensity is seen, the reaction can be deemed complete.

As used herein, "formazan" refers to the colored compound formed by the reduction of a water soluble tetrazolium salt. There are many forms of tetrazolium salts and their formazan products vary in color and in their ability to bond with protein. The presently preferred formazan is the reduction product of nitro blue tetrazolium (2,2'di-p-nitrophenyl-5,5'-diphenyl-3,3'-(3,3'-dimethoxy-4,4'-biphenyl) ditetrazolium chloride). The formazan compound from this tetrazolium salt has an intense blue-purple color. It has two nitro groups which are believed to facilitate its binding to protein molecules.

Formazan compounds can be formed in a solution containing a water-soluble tetrazolium salt by elevating the pH of the solution to 10 or above, or by the additon of a reducing agent such as sodium ascorbate at a pH of about 7.4, or through a biochemical reaction catalyzed by certain enzymes, such as oxidases, dehydrogenases or diaphorases.

The prelabeled primary antibody may be labeled either directly or indirectly. If direct, the formazan is bonded to or absorbed directly onto the primary antibody. If indirect, the formazan is bonded or absorbed onto a secondary protein which in turn is conjugated with the primary antibody.

For example, formazan particles may be absorbed onto a secondary antibody which can then be conjugated to the primary antibody by conventional methods. The benefit of such a technique is that a particular secondary antibody may be able to be conjugated to a variety of primary antibodies. Accordingly, a single stock of the prelabeled secondary antibody may be used in labeling a variety of primary antibodies.

As another example, it is well known that avidin has a strong affinity for biotin and that biotin is able to be conjugated with a variety of antibodies, the conjugate typically involving several biotin molecules per antibody. Accordingly, avidin molecules may be prelabeled with formazan and then reacted with biotinylated primary antibody, i.e., biotin-primary antibody conjugate, to form the prelabeled primary antibody. Again the benefit of this method is that a variety of primary antibodies can be conjugated with biotin, hence a variety of primary antibodies can be prelabeled with the use of a single stock solution of prelabeled avidin. Moreover, since several biotin molecules typically bind with an antibody, the primary antibody can be labeled with more formazan than otherwise possible by the direct method. This intensifies the color of the primary antibody reactant and thus increases the sensitivity of the test.

As yet another example, it is well known that protein A will bond to the $F_c$ portion of a variety of primary antibodies. Accordingly, protein A can be prelabeled with formazan and then reacted with the primary antibody to form the prelabeled primary antibody.

There are several ways in which the formazan particles can be combined with a protein substrate whether that be the primary antibody or a secondary protein such as a secondary antibody, avidin or protein A or mixtures thereof which is then conjugated with the primary antibody.

The simplest method is to simply mix previously formed formazan particles with a solution containing the protein substrate. Formazan particles demonstrate an affinity for protein substrates and will selectively bond to the protein substrates. This method is not preferred because the affinity of formazan for protein substrates is non-selective and therefore any protein substrate in the solution may become labeled with the formazan particles. in addition, formazan particles tend to form agglomerations which may become so large that when bonded to the protein substrate, they may hinder the ability of the protein substrate to bond to the antigen. This method also tends to yield a large amount of unreacted formazan which creates an undesirably intense background color.

A more preferred method of combining the formazan particles with a protein substrate is to reduce the tetrazolium salt and thus form the formazan particles in the presence of the protein substrate. In this method, formazan particles bond to the protein substrate immediately upon formation. When bound to the protein substrate, the formazan particles tend to remain microcrystalline and not form large troublesome aggregates. Less unbound formazan is generated by this method.

The presently preferred method of combining formazan particles with a protein substrate is to first conjugate the protein substrate with an enzyme such as an oxidase, dehydrogenase or diaphorase, capable of reducing the tetrazolium salt either directly or indirectly. In this procedure, the protein substrate—enzyme conjugate is mixed with a solution of the tetrazolium salt and the tetrazolium salt is reduced to the formazan by the enzyme. This method appears to generate the least unbound formazan and thus creates the least amount of background color.

For example, a convenient method is to add the appropriate substrates, e.g., in the case of glucose oxidase, they are 30 mg/ml glucose, 0.4 mg/ml phenazine methosulfate and 1.5 mg/ml nitro blue tetrazolium, to reactants which have been conjugated to glucose oxidase. If the enzyme/substrate mixture is vortexed immediately, the newly formed formazan particles will adhere to the nearest protein molecule, including the enzyme itself.

The binding of formazan to protein is believed to be proportional to the number of nitro groups on the formazan molecule as well as the structure of the protein molecule. While the chemical relationship between the formazan and the protein is not well understood, the binding is thought to occur at tyrosine residues. The formazan affinity for commonly used proteins in immunoassays, is greatest for albumin and immunoglobulins, less for avidin and glucose oxidase, and least for protein A, unless it is conjugated to glucose oxidase.

Once the formazan-labeled antibody has been prepared, it may be used immediately or stored. If stored, the formazan-labeled antibody (or other formazan-labeled protein) must be stored in the dry state. Simple air drying of the formazan-labeled antibody may be used. However, this drying method is not preferred as the formazan particles tend to form agglomerations during the lengthy drying period. The preferred drying method is by convention lyophilization. It has also been found that a small amount of mannitol (e.g., 20 mg/mg protein) added to the solution of formazan-labeled antibody before lyophilization facilitates redissolving of the formazan-labeled antibody.

The dipstick is prepared by conventional methods. For example, in one such method, a nitrocellulose membrane is mounted at the lower end of the dipstick. A solution containing nonlabeled primary antibody is applied over one section of the membrane to bind primary antibodies to the membrane. A solution containing a blocking agent, e.g., 1% serum albumin, which bonds to the membrane and prevents subsequent bonding of the primary protein to the membrane.

The dipstick procedure described above includes the use of a formazan-labeled antibody. It is to be understood that other protein-specific dyes may be used. Other dyes applicable to the present invention include, but are not restricted to, Coomassie blue, amido black, toluidine blue, fast green, india ink, silver nitrate and silver lactate.

It is also apparent that the prelabeled primary protein reactant is not limited to antibodies. Any protein having a specific affinity for a second protein may be used in this method to detect that second protein.

The advantages of the above-described dipstick procedure are apparent. It provides a simple, virtually foolproof procedure for detecting a particular antigen or other protein. All one needs to do is to dissolve the prelabeled protein reagent with the test fluid, insert the dipstick and wait for color development.

The simplicity and accuracy of the procedure makes it ideal for use as a home pregnancy test where the test fluid is urine. It is also ideal for field tests of farm animals for infectious agents as performed by USDA inspectors. Such simplicity and accuracy also make the procedure ideal for use in clinic or a doctor or veterinarian's office to test for such things as the presence of AIDS virus, herpes simplex, tumors, viral infections, bacterial infections, and a variety of other ailments manifested by the presence of a particular antigen or other protein.

In addition to the simplicity and accuracy of the procedure, the rapidity in which the procedure can be run makes it ideal for use in hospitals and laboratories engaged in batch testing of numerous specimens for the presence of an antigen.

It is apparent that the present invention is not limited to the dipstick procedure described above. For example, it is apparent that, if a solid substrate is used to separate the reacted prelabeled protein from the reaction mixture, solid substates other than dipsticks may be used. As an illustration, antibodies may be bonded to the floor of microtiter wells and the test fluid and prelabeled-antibodies added to the wells. After a select period, the wells are washed and the color developed on the floor of the wells from the antibody-antigen reaction examined. By use of an automatic reader, the results of numerous tests can be determined in a few minutes.

Separation of the recited prelabeled protein from unreacted dye and unreacted prelabeled protein need not involve a solid substrate such as a dipstick or the floor of a microtiter well. For example, a prelabeled proteins of the present invention can be used to detect specific markers on cells in a tissue section. This would enable a pathologist to spot individual cancer cells in a field of normal cells, to determine what type of cells produce a particular antigen, to identify early stages of tumor cell transformation or to identify specific cell types, e.g., to recognize and distinguish subsets of T lymphocytes.

In such a procedure, the tissue section or other sample is simply incubated with a prelabeled protein having a specific affinity for the antigen, cell marker or the like to be detected. Any unreacted prelabeled protein is washed from the sample which is then examined to see if and where the prelabeled protein has bonded to the sample.

EXAMPLE I

Binding of formazan to immunological reactants was accomplished by three separate methods. In the first, formazan is formed by the addition of 0.3 ml 5N NaOH to 2.0 ml phosphate buffered saline (PBS) solution at pH 7.4 containing 3.0 mg nitro blue tetrazolium. The formazan was pelleted by centrifugation, washed twice with 10 ml of PBS solution. The formazan particles were resuspended in 0.5 ml of PBS. The formazan suspension was mixed with 0.5 ml of a 1 mg/ml avidin solution. Binding was accomplished by simple adsorption. A dipstick comprising a nitrocellulose membrane on which biotinylated immunoglobin was adsorbed over a first section and a section free of biotinylated immunoglobin and blocked to prevent adsorption of biotinylated immunoglobin was prepared and immersed in the formazan-avidin mixture. Binding of the formazan-labeled avidin to the biotinylated immunoglobin was demonstrated by a greater color intensity across the first section of the membrane as compared to the second. A heavy background color was developed.

EXAMPLE II

In the second procedure, a mixture of 0.01 ml avidin solution containing 1 mg/ml avidin and 0.01 ml nitro blue tetrazolium solution containing 3 mg/ml nitro blue tetrazolium (NBT) was diluted with 0.1 ml PBS. The nitro blue tetrazolium was reduced in the presence of the avidin by the addition of 0.01 ml of a 5 mg/ml solution of sodium ascorbate at pH 7.4. The dipstick procedure of Example I was repeated. Specific avidin adsorption on the biotinylated immunoglobin was demonstrated again by a greater color intensity over the first membrane section when compared to the second. As compared to the results of Example I, the background color was reduced.

EXAMPLE III

In the third procedure, 0.01 ml of a stock nitro blue tetrazolium (NBT) solution (30 mg glucose, 0.4 mg phenazine methosulfate and 1.5 mg NBT/ml PBS) was mixed quickly into 0.26 ml of solution containing 0.1 mg/ml avidin-glucose oxidase conjugate. Enzymatic reduction of the nitro blue tetrazolium in the presence of the avidin conjugate resulted. The dipstick procedure of Example I was again followed. The results showed a marked increase in the difference in color intensity between the first and second sections of the membrane. Here, the background color was negligible.

EXAMPLE IV

A commonly used amplification system was tested for the signal-to-noise ratio, using the conventional ELISA procedure in comparison to the preformed formazan method of Example III. Glucose oxidase-conjugated avidin concentrate (2.5 mg/ml) was diluted 1:25 in two aliquots with PBS. A 0.01 ml volume of stock nitro blue tetrazolium solution was added to one aliquot to allow formazan labeling of the avidin. Dipsticks, whose membranes were dotted with 0.7 ug/0.001 ml biotinylated goat anti-mouse IgG over a first section and blocked with 1% rabbit serum albumin over a second section, were incubated at room temperature in each of these aliquots for 40 minutes. At the end of this period, the dipstick from the first aliquot containing the preformed formazan mixture was removed, blotted and air-dried. The dipstick from the second aliquot containing the nonlabeled avidin-enzyme conjugate was washed, then stained in the nitro blue tetrazolium solution for three minutes. The excess nitro blue tetrazolium solution was removed by a second washing procedure, then the dipstick was blotted and air-dried. The optical density of the dot from the post-stained procedure was 0.45, but the background had an optical density of 0.35, giving a net signal of 0.10. By way of comparison, the dot from the formazan-labeled avidin had an optical density of only 0.25, but had a low background density of only 0.02. This gave a net reading of 0.23, which was more than twice the net reading of the conventional procedure, with less time and handling involved.

EXAMPLE V

Detection of an antigen (mouse IgG) was demonstrated in the following procedure. Materials were prepared prior to the reaction, as follows: Dots of goat anti-mouse IgG antiserum were placed on nitrocellulose membranes mounted on plastic dipsticks. The surrounding membranes were blocked with 1% normal human serum in phosphate buffered saline. These membranes were allows to air dry until use. A volume of 0.01 ml of a stock nitro blue tetrazolium solution was added to each of 0.25 ml aliquots of a 1:25 dilution of a glucose oxidase-conjugated goat anti-mouse IgG antiserum in PBS (tinal concentration was 10 ug/0.25 ml). These aliquots were quickly vortexed, then left undisturbed for five minutes, during which formazan formed and bound to the protein constituents.

The actual reaction occured by the addition of the antigen (mouse IgG) at different concentrations to each aliquot of formazan-labeled antibody, then inserting a dipstick into each reaction vessel. The reaction resulted in a sandwich of membrane-bound antibody : antigen : formazan-labeled antibody. A well-defined dot could be visualized after 15 minutes of incubation at room temperature with antigen concentrations of 3.6 ug/ml or more. The reactions were allowed to proceed for 40 minutes, then the dipsticks were removed, blotted on tissue paper and air-dried. The optical density of the dots were read with a reflecting densitometer. Antigen concentrations of 36, 3.6, 0.36 and 0 ug/ml showed net optical density measurements (above background readings) of 0.16, 0.15, 0.02 and 0, respectively, Under these conditions, the sensitivity of the system permitted detection of 90 ng of antigen in the 0.25 ml reaction volume.

EXAMPLE VI

Detection of an antigen (mouse IgG) was further demonstrated in the following procedure.

A volume of 0.025 ml biotinylated anti-mouse IgG antibody (0.69 mg/ml) was diluted with 0.020 ml phosphate buffer solution and mixed with 0.01 ml glucose oxidase conjugated avidin (0.25 mg/ml). Then 0.01 ml stock nitro blue tetrazolium solution as added for formazan development over a 10 minute interval. Finally, 0.01 ml antigen (5 ug/ml mouse IgG) was added and a dipstick, dotted with anti-mouse IgG antibody and blocked with 1% human serum was inserted. The reaction mixture was incubated at room temperature for one hour, then the dipstick was removed, blotted and air-dried. The net optical density of the dot was 0.29. A comparable test, but without the addition of antigen, showed no evidence of color development over the dot. The same mixture of prelabeled reactants gave positive reactions to 0.5 ng of antigen (mouse IgG) and above when dotted on nitrocellulose membranes and blocked with 1% normal human serum.

It is apparent that the foregoing description should not be read as pertaining only to the precise compositions and procedures described, but rather should be read consistent with and as support for the following claims which are to have their fullest fair scope.

What is claimed is:

1. A method for detecting the presence of target proteins in a test fluid comprising:
   mixing a sample of the test fluid with a solution free of target proteins and containing a primary protein having a specific affinity for the target protein which has been prelabeled with formazan for a time sufficient to form a colored reaction product between the prelabeled primary proteins and any target proteins in the test fluid;
   separating any formed reaction product from unreacted prelabeled primary proteins; and
   visually detecting the presence of any formed reaction product.

2. A method as claimed in claim 1 wherein the formed reaction product is separated from unreacted prelabeled primary proteins remaining in the mixture by immersing into the mixture a solid substrate having said primary proteins not labeled with formazan bonded to the surface of the solid substrate for a time sufficient for the formed reaction product to bind to the nonlabeled primary proteins bound to the solid substrate and then withdrawing the solid substrate from the mixture.

3. A method as claimed in claim 2 wherein the solid substrate comprises a first section on which said nonlabeled primary proteins are bonded and a second section free of said primary proteins and which is blocked to prevent bonding of said primary proteins.

4. A method as claimed in claim 3 wherein the solid substrate further comprises a third section on which said target proteins are bonded.

5. A method as claimed in claim 1 wherein said target protein is a antigen and the primary protein is an antibody having a specific affinity for that antigen.

6. A method as claimed in claim 1 wherein the target protein is selected from the group consisting of beta-human chorionic gonadotropin hormone, HTLV III virus, herpes simplex type II virus, streptococcus A, feline leukemia virus, psittacosis, nuclear antigens, thyroidal antigens, mitochondrial antigens, smooth muscle antigens, treponema pallidum, cytomegalo virus, and tumor cell markers.

7. A dipstick immunodot procedure for detecting the presence of a target protein in a test fluid comprising:
 mixing the test fluid with a solution containing primary proteins having a specific affinity for the target protein, said primary proteins being prelabeled with formazan;
 immersing into the mixture a dipstick on which is mounted a membrane having a first section on which said primary proteins not prelabeled with formazan are bonded and a second section free of said primary proteins and which is blocked to prevent bonding of said primary proteins;
 removing the dipstick from the mixture after a select period of time; and
 visually comparing the intensity of color on the first section of the dipstick membrane with the intensity of color on the second section of the dipstick membrane.

8. A procedure as claimed in claim 7 wherein the dipstick further comprises a third section on which said target proteins are bonded.

9. A procedure as claimed in claim 7 wherein said target protein is an antigen and the primary protein is an antibody having a specific affinity for the antigen.

10. A prelabeled immunological reactant for use in detecting the presence of a select target protein in a test sample comprising a primary protein having a specific affinity for the select target protein and formazan bound to the primary protein.

11. A reactant as claimed in claim 10 wherein formazan is bound directly to the primary protein.

12. A reactant as claimed in claim 10 wherein formazan is bound to a secondary protein which is conjugated to the primary protein.

13. A reactant as claimed in claim 12 wherein the secondary protein is protein A.

14. A reactant as defined in claim 12 wherein the secondary protein is avidin and the primary protein is first conjugated with biotin and then conjugated with the formazan-labeled avidin.

15. A prelabeled immunological reactant for use in detecting the presence of a specific target protein in a test sample comprising a formazan-labeled primary protein wherein formazan is bound directly or indirectly to the primary protein prepared by mixing a solution of the primary protein and a water soluble tetrazolium salt and then reducing the tetrazolium salt in the presence of the primary protein.

16. A reactant as defined in claim 15 wherein the formazan is bound directly to the primary protein and the tetrazolium salt is reduced enzymatically by an enzyme conjugated to the primary protein.

17. A reactant as claimed in claim 15 wherein the formazan is bound to a secondary protein which is conjugated to the primary protein and the tetrazolium salt is reduced enzymatically by an enzyme conjugated to the secondary protein.

18. A reactant as claimed in claim 17 wherein the secondary protein is selected from the group consisting of avidin, protein A, secondary antibodies having a specific affinity for the primary antibody, and mixtures thereof.

* * * * *